(12) United States Patent
Power et al.

(10) Patent No.: US 6,915,962 B2
(45) Date of Patent: Jul. 12, 2005

(54) APPARATUS FOR PROVIDING AEROSOL FOR MEDICAL TREATMENT AND METHODS

(75) Inventors: John Power, Galway (IE); Des Regan, Galway (IE); Niall Smith, Galway (IE)

(73) Assignee: Aerogen, Inc., Mountain View, CA (US)

( * ) Notice: Subject to any disclaimer, the term of this patent is extended or adjusted under 35 U.S.C. 154(b) by 0 days.

(21) Appl. No.: 10/443,114

(22) Filed: May 20, 2003

(65) Prior Publication Data

US 2004/0050947 A1 Mar. 18, 2004

Related U.S. Application Data

(60) Provisional application No. 60/382,256, filed on May 20, 2002.

(51) Int. Cl.[7] ................................................. B05B 1/08
(52) U.S. Cl. ..................... 239/102.2; 552/596; 552/601
(58) Field of Search ...................... 239/4, 102.1, 102.2, 239/552, 596, 601, DIG. 19; 128/200.14, 200.16; 264/259, 328.2

(56) References Cited

U.S. PATENT DOCUMENTS

| | | | |
|---|---|---|---|
| 5,152,456 A | | 10/1992 | Ross et al. |
| 5,248,087 A | | 9/1993 | Dressler |
| 5,261,601 A | * | 11/1993 | Ross et al. ............... 239/102.2 |
| 5,516,043 A | | 5/1996 | Manna et al. |
| 5,518,179 A | | 5/1996 | Humberstone et al. |
| 5,823,428 A | * | 10/1998 | Humberstone et al. ..... 239/601 |
| 5,938,117 A | * | 8/1999 | Ivri .......................... 239/102.2 |
| 6,062,212 A | * | 5/2000 | Davison et al. ......... 128/200.16 |
| 6,394,363 B1 | * | 5/2002 | Arnott et al. ............. 239/102.1 |
| 6,402,046 B1 | * | 6/2002 | Loser ....................... 239/102.2 |
| 6,443,366 B1 | * | 9/2002 | Hirota et al. ............. 239/102.2 |
| 6,554,201 B2 | * | 4/2003 | Klimowicz et al. ...... 239/102.1 |

* cited by examiner

*Primary Examiner*—Steven J. Ganey
(74) *Attorney, Agent, or Firm*—Townsend and Townsend and Crew LLP (57) ABSTRACT

Embodiments of the present invention include apparatus and methods for aerosolizing liquid. One embodiment of the invention provides an apparatus for generating an aerosol. The apparatus includes an actuator having a first face and a second face and defining an opening therethrough, as well as a vibratory element in mechanical communication with the actuator, and a sealing member configured to isolate the vibratory element from a surrounding environment. In accordance with certain embodiments, the apparatus further comprises an aerosolization element mounted on the actuator and disposed substantially over the opening, wherein the aerosolization element defines at least one aperture therethrough. Hence, the vibratory element may be operated to vibrate to cause movement of the aerosolization element in such a manner that a liquid at the first face of the aerosolization element can be dispensed as an aerosol through the at least one aperture. Some embodiments feature an electrode coupled to the vibratory element.

27 Claims, 10 Drawing Sheets

APPARATUS FOR PROVIDING AEROSOL FOR MEDICAL TREATMENT AND METHODS

CROSS-REFERENCES TO RELATED APPLICATIONS

This application is a nonprovisional of provisional U.S. Patent App. Ser. No. 60/382,256, entitled "APPARATUS AND METHODS OF PROVIDING AEROSOL FOR MEDICAL TREATMENT," filed May 20, 2002 by Power et al., the entire disclosure of which is incorporated herein by reference for all purposes.

BACKGROUND OF THE INVENTION

This invention relates generally to the field of pulmonary drug delivery, and in particular to the aerosolizing of liquid medicament into fine liquid droplets for inhalation.

In the fields of drug delivery and pulmonary therapy, the aerosolization of drugs and other medicaments for pulmonary delivery can provide significant therapeutic benefits. To realize those benefits, there have arisen a variety of atomizers and nebulizers, which can vary significantly in methods of operation. For instance, some aerosol generators operate by vibrating at a relatively high frequency an aperture plate in contact with the material to be aerosolized. By way of example, U.S. Pat. Nos. 5,164,740; 5,586,550; 5,758,637; and 6,235,177, the complete disclosures of which are herein incorporated by reference for all purposes, describe exemplary devices for producing fine liquid droplets in such a fashion. Such devices have proven to be tremendously successful in aerosolizing liquids. Another technique for aerosolizing liquids is described in U.S. Pat. No. 5,261,601, also incorporated herein by reference for all purposes, and utilizes a perforate membrane disposed over a chamber. The perforate membrane comprises an electroformed metal sheet using a "photographic process" that produces apertures with a cylindrical exit opening.

Commonly, such aerosol generators-operate by using a vibratory element to drive an aerosolizing element (e.g., aperture plate, membrane, etc.). In many cases, the vibratory element comprises a piezoelectric and/or piezomagnetic material such as one of many ceramics known in the art to exhibit such properties. When excited by the appropriate field, the piezo will expand/contract, such that application of an oscillating field can produce oscillating vibration of the piezo (and, by extension, the aerosolizing element) at a frequency related to that of the oscillating field. Often, the field will be applied to the piezo through one or more electrodes in electrical communication with the piezo.

In use, aerosol generators can be subjected to a variety of environmental conditions, many of which can threaten to degrade the performance of the generator; for instance, during operation, the piezo and/or the electrodes may be in danger of exposure to the fluid being aerosolized. Those skilled in the art will recognize that, in many cases, prolonged exposure to such fluids can result in corrosion of the piezo and/or the electrodes, and even relatively brief exposure can vitiate the electrical communication between the piezo and the circuitry by which it is driven (for example, by short-circuiting the electrodes and/or otherwise interfering with the electrical communication between the electrodes and the piezo).

Likewise, various cleaning procedures can prove harmful to the operation of the aerosol generator if care is not taken. For instance, in many cases aerosol generators are used in hospitals and/or other institutional settings, where strict sanitization policies often are enforced to prevent cross-infection by multiple users of a generator. Merely by way of example, aerosol generators may be exposed to potentially corrosive substances, such as solvents and disinfectants. In addition, generators may be exposed to relatively high levels of heat, pressure, and/or humidity during sanitization processes, such as autoclaving and the like. Without protection, therefore, the relatively sensitive components of aerosol generators (including, for example, their piezos and/or electrodes) may be damaged during sanitization and/or the operational lives of such components may be limited significantly by repeated sanitization procedures.

BRIEF SUMMARY OF THE INVENTION

Embodiments of the invention, therefore, address certain limitations in the prior art and include apparatus and methods for aerosolizing liquid. For instance, one embodiment of the invention provides an apparatus for generating an aerosol. The apparatus includes an actuator having a first face and a second face and defining an opening therethrough, as well as a vibratory element in mechanical communication with the actuator, and a sealing member configured to isolate the vibratory element from a surrounding environment. In accordance with certain embodiments, the apparatus further comprises an aerosolization element mounted on the actuator and disposed substantially over the opening, wherein the aerosolization element defines at least one aperture therethrough. Hence, the vibratory element may be operated to vibrate to cause movement of the aerosolization element in such a manner that a liquid at the first face of the aerosolization element can be dispensed as an aerosol through the at least one aperture. Some embodiments feature an electrode coupled to the vibratory element.

In accordance with certain embodiments, the vibratory element is annular in shape and/or comprises a piezoelectric ceramic In other embodiments, the sealing element is annular, such that it covers at least a portion of the first face of the actuator, at least a portion of the second face of the actuator, and at least a portion of the vibratory element. In further embodiments, the sealing element can comprise an elastomer and/or a rubber, which can be, merely by way of example, a synthetic rubber or a silicone. The sealing member can be molded around at least a portion of the vibratory element, and can be formed by injection molding.

Some embodiments include one or more layers of bonding material between the sealing element and the vibratory element. The bonding material can couple the sealing member relatively securely to at least one of the vibratory element and the actuator and can, in some cases, provide a relatively impervious barrier between the electrode and the surrounding environment. The bonding material can be relatively impervious to a relatively severe environmental condition, which can include, inter alia, heat, humidity, pressure, alternating cycles of vacuum and pressure, and a corrosive chemical.

In other embodiments, the bonding material can be selected from the group consisting of a paint, an epoxy, an adhesive and a primer, and the at least one layer of bonding material can comprise a first application of a first bonding material and a second application of a second bonding material. The first and second bonding materials can be the same bonding material. In further embodiments, the bonding material comprises an adhesive situated between the vibratory element and the actuator. In some cases, the vibratory element comprises an inner surface and an outer surface, and the adhesive can be situated between the sealing element and at least a portion of at least one of the inner and outer surfaces of the vibratory element.

Other embodiments of the invention provide methods of making and/or using aerosol generator assemblies. One exemplary method for making an aerosol generator assembly comprises providing an aerosol generator, which can be similar to one of the aerosol generators discussed above. The method also includes providing a mold assembly formed to receive the aerosol generator, placing a mold material into the mold assembly, allowing mold material to form a sealing element about at least a portion of the aerosol generator and removing the aerosol generator from the mold assembly.

In some cases, placing the mold material into the mold assembly comprises injection molding the mold material. In other cases, the method includes preparing at least one of the vibratory element and the actuator. Preparing the vibratory element and/or actuator can comprise chemical etching of those components.

In certain embodiments, the method further comprises applying at least one layer of bonding material between the mold material and least one of the vibratory element and the actuator. Applying at least one layer can include applying a layer of a first bonding material and applying a layer of a second bonding material. The first bonding material and the second bonding material can be the same bonding materials. One or more layers can be applied at room temperature and cured at a relatively high temperature for a specified period of time. The relatively high temperature is above about 100 degrees C., more specifically between about 100 degrees C. and about 150 degrees C. In some cases, the relatively high temperature is between about 120 degrees C. and about 140 degrees C., and more specifically, about 130 degrees C. In other cases, the specified period of time is between about 15 minutes and about 45 minutes.

BRIEF DESCRIPTION OF THE DRAWINGS

A further understanding of the nature and advantages of the present invention may be realized by reference to the figures which are described in remaining portions of the specification. In the figures, like reference numerals are used throughout several to refer to similar components. In some instances, a sub-label consisting of a lower case letter is associated with a reference numeral to denote one of multiple similar components. When reference is made to a reference numeral without specification to an existing sub-label, it is intended to refer to all such multiple similar components.

DETAILED DESCRIPTION OF THE INVENTION

Embodiments of the present invention include apparatus and methods for aerosolizing liquid. In accordance with one embodiment, an aerosol generator assembly is provided, comprising an aerosol generator and a sealing element overmolded onto the aerosol generator. Those skilled in the art will appreciate that, in accordance with certain embodiments of the invention, an aerosol generator comprises a piezoelectric and/or piezomagnetic vibratory element (a "piezo") for vibrating an aerosolization element to aerosolize a fluid. In many cases, the piezoelectric member is driven by application of an electric and/or magnetic field, which often is supplied through an electric circuitry coupled to the piezo by one or more electrodes. The connection between the circuitry and the electrodes can be of any type that is operative to supply electric current to the piezo, including, for instance, conductive metal wires (optionally, with non-conductive insulation), conductive polymeric materials, and the like.

In accordance with some embodiments of the invention, a sealing member, which can comprise a variety of relatively impermeable and/or elastic substances (including, merely by way of example, elastomers, rubbers (both natural and synthetic), urethanes, silicon and the like) and can serve to isolate/protect the piezo and/or electrodes from the surrounding environment, which can sometimes include relatively severe environmental conditions, including without limitation, the conditions described below, such as relatively high heat, pressure, and atmospheric moisture, immersion in fluids, exposure to corrosive fluids, and the like.

Merely by way of example, a sealing member in accordance with some embodiments comprises a thermoplastic elsastomer known in the art as Santoprene™, which is commercially available from Advanced Elastomer Systems, L.P., of Akron, Ohio, USA. As described below, the sealing member can be formed by a variety of techniques, including for example, injection molding. U.S. Pat. No. 6,554,201, the entire disclosure of which is incorporated herein by reference for all purposes, describes one exemplary injection molding process that can be used in conjunction with aerosol generators.

In other embodiments, the sealing member can be used as a mounting apparatus for coupling the aerosol generator to a housing. Those skilled in the art will recognize that aerosol generators often are mounted within a housing for operation, such that the housing can provide (and/or be in communication with) a supply of fluid to be aerosolized, such as a chamber and/or the like. Additionally, the housing can also be an integrated part of a nebulizer system, such that it provides fluid communication between the aerosol generator and a patient's airway, either passively (such as, for instance, in an inhaler, where the patient inhales the aerosolized fluid from the housing) and/or actively (such as, for instance, when the housing is part of a respirator system). In some embodiments, therefore, the sealing member, which, as noted, can comprise a relatively elastic and/or flexible substance, can couple the aerosol generator to the housing securely enough to prevent dislodging of the generator, yet flexibly enough that the vibratory characteristics of the generator are not significantly impacted, thereby substantially maintaining the performance of the aerosol generator.

In still other embodiments, one or more bonding materials can be applied between and/or among the sealing member and various components of the aerosol generator. In some cases, bonding materials can include adhesives, epoxies, paints, primers and the like. Those skilled in the art will recognize that certain bonding materials can provide a relatively secure coupling between the aerosol generator and the overmold. Further, the bonding materials can be selected based on their abilities to enhance the vibratory performance of the generator and/or create or reinforce a barrier between the piezo (and/or its electrodes) and the surrounding environment. In many cases, the bonding materials are relatively impervious to environmental conditions to which aerosol generators commonly are exposed during operation, sanitization, etc. For instance, as discussed below, certain bonding materials can be relatively immune to an autoclave environment, which can introduce significantly elevated heat and pressure, along with relatively high levels of atmospheric water vapor and/or other fluids. Likewise, certain bonding materials can be impervious to any corrosive effects of cleaning fluids and/or fluids to be aerosolized.

Figure 1:
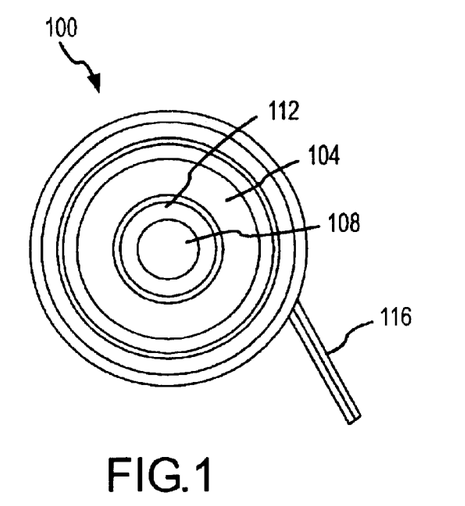
FIG. 1 is a plan view of an aerosol generator assembly, in accordance with various embodiments of the present invention.
Figure 2:
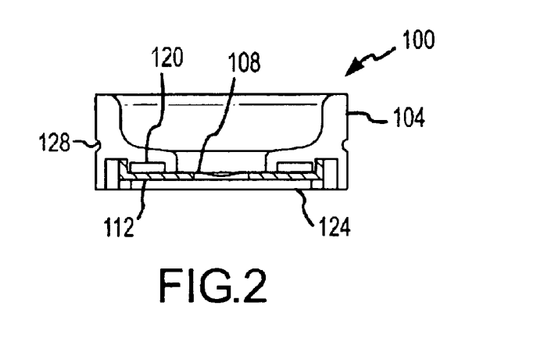
FIG. 2 a side cross-sectional view of an aerosol generator assembly, in accordance with various embodiments of the present invention.

Turning now to FIG. 1, a top view of an aerosol generator assembly 100, including a sealing member 104, is illustrated, in accordance with certain embodiments of the invention. The aerosol generator assembly 100 further includes an aerosolization element 108, an actuator 112, and one or more electrical conduits 116. As illustrated by FIG. 2, a cross-sectional diagram of the assembly 100, an aerosol generator can further include a piezoelectric member 120, as well as a bottom plate 124. Although not apparent in the cross-sectional illustration of FIG. 2, those skilled in the art will appreciate from the view of FIG. 1 that the actuator 112 can be annular in shape, thereby describing a central aperture, with the aerosolization element 108 bonded to the inner portion of the annular actuator 112 and spanning the central aperture. Likewise, the piezo 120 can be annular in shape and can be bonded to a central and/or outer portion of the actuator 112.

Also as illustrated by FIG. 2, the sealing member 104 can be formed in such a fashion as substantially to surround the piezo 120 and actuator 112, and can, as illustrated in FIG. 1, be cup-shaped and/or annular in shape as well. Thus, in some embodiments, the sealing member 104 can be formed to have a relatively thick exterior portion that tapers to a relatively narrow interior portion, which can allow for more secure mounting in a housing without impacting the ability of aerosolized liquid to disperse away from the aerosolization element 108. To further facilitate mounting, the sealing member 104 can include one or more features (which may be integrally formed with the sealing member 104) to allow efficient coupling of the assembly 100 with the housing. Merely by way of example, the sealing member 104 of FIG. 2 includes a notch 128, which can be used for this purpose, in its exterior circumference.

Figure 3:
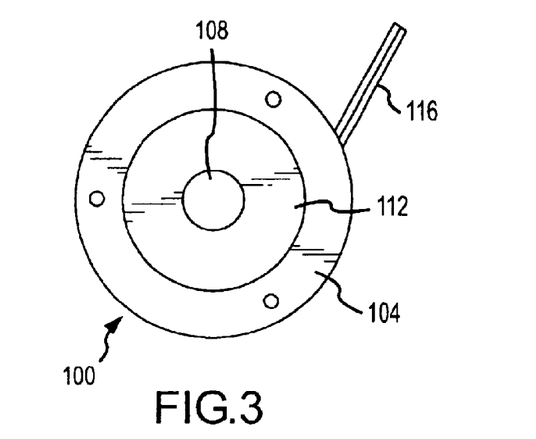
FIG. 3 is a bottom view of an aerosol generator assembly, in accordance with various embodiments of the present invention.

FIG. 3 illustrates a bottom view of the aerosol generator assembly 100. As illustrated by FIG. 3, in accordance with certain embodiments, the sealing member 104 can extend around the outer surface of the generator to encompass a portion of the bottom face of the aerosol generator. In some cases, a portion of bottom face of the actuator 112 may be left exposed, while in other cases, the sealing member 104 may extend inward across the bottom of the generator toward the actuator's central aperture, leaving only the aperture plate 108 exposed. Also as shown on FIG. 3, the sealing member 104 may be formed to allow insertion of one or more electrical conduits 116 (e.g., insulated wires, etc.) through the sealing member 104 for coupling to a piezo, one or more electrodes, etc. In alternative embodiments, the electrical conduits 116 can be attached to the aerosol generator before formation of the sealing member 104, such that the sealing member 104 is molded around the conduits 132.

Figure 4:
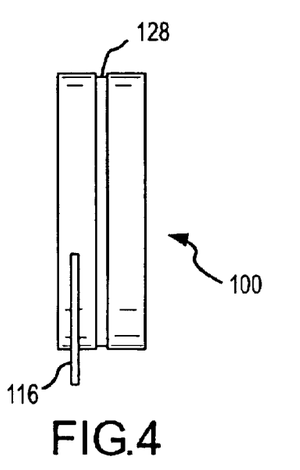
FIG. 4 is a side view of an aerosol generator assembly, in accordance with various embodiments of the present invention.
Figure 5:
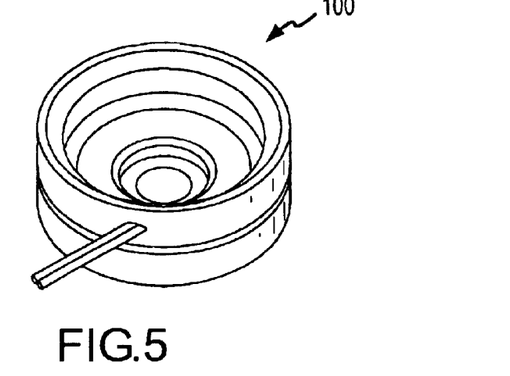
FIG. 5 is a top perspective view of an aerosol generator assembly, in accordance with various embodiments of the present invention.
Figure 6:
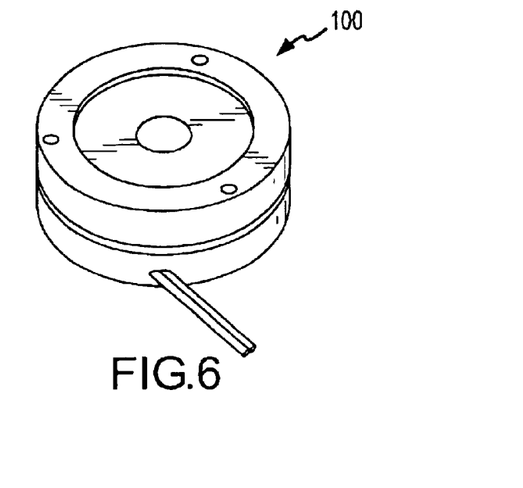
FIG. 6 is a bottom perspective view of an aerosol generator assembly, in accordance with various embodiments of the present invention.

FIG. 4 illustrates a side view of the aerosol generator assembly 100, displaying the circumferential notch 128 described above, as well as the electrical conduits 132. FIGS. 5 and 6 illustrate perspective drawings of the assembly 100, as seen from the top and bottom, respectively.

Figure 7:
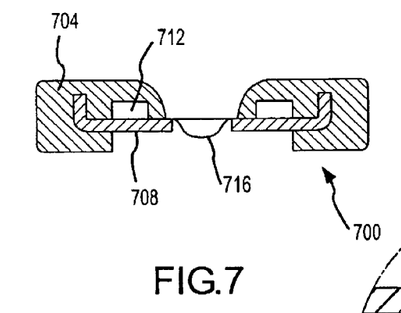
FIG. 7 illustrates an aerosol generator assembly in accordance with various embodiments of the invention.

FIG. 7 provides a cross-sectional illustration of an aerosol generator assembly 700 in accordance with other embodiments of the invention. The aerosol generator assembly 700 includes a sealing member 704 formed around an actuator 708 and a vibratory element 712 in mechanical communication with one another. The assembly 700 further includes an aerosolization element 716 mounted on the actuator 708 in a fashion similar to that described above. The sealing member 704 is generally annular in shape.

Figure 8A:
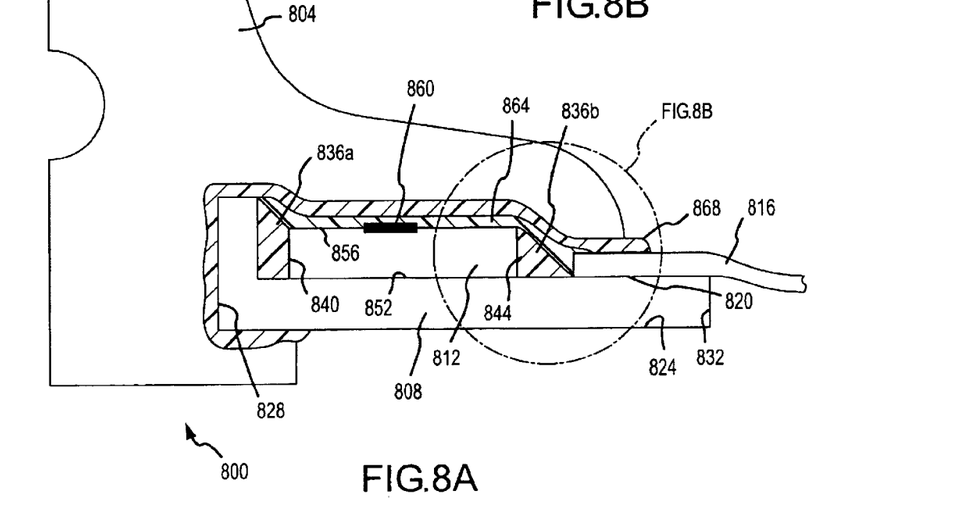
FIGS. 8A and 8B illustrate a portion of an aerosol generator assembly with a plurality of layers of bonding materials, in accordance with various embodiments of the invention.

FIG. 8A illustrates a cross-sectional view of an aerosol generator assembly 800 in accordance with some embodiments of the invention. The assembly 800 features a sealing member 804 molded around an aerosol generator, which includes an actuator 808 in mechanical communication with a piezoelectric vibratory element 812. An aerosolization element 816 can be mounted on the actuator 808 and can be used to aerosolize a liquid in a manner similar to that discussed above. The actuator has a first face 820 and a second face 824. The actuator 808 can be annular, having an outer surface 828 and an inner surface 832, which can define a central aperture through the actuator 808. In some cases, the outer surface 828 can define a flange. The aerosolization element 816 can be mounted so as to cover substantially the central aperture, and the aerosolization element 816 itself can have one or more apertures through which the aerosolized material can flow.

The vibratory element 812 can be in mechanical communication with the actuator 808. For instance, the vibratory element 812 can be mechanically coupled to the actuator 808 through a variety of means. Merely by way of example, the vibratory element 812 can be bonded to the actuator 808 with an adhesive 836. For instance, in some cases, the vibratory element 812 may be attached with mechanical fasteners to the actuator 808. In other cases, the vibratory element 812 and the actuator 808 may be integrally formed, perhaps from the same material. In certain embodiments, as shown in FIG. 8A, the vibratory element 812 may be configured in a ring of rectangular cross-section, having an outer surface 840 and an inner surface 844, and the adhesive can be placed adjacent to either surface 840, 844, or both, to provide mechanical coupling between the vibratory element 812 and the actuator 808. The vibratory element can also have a first face 852 and a second face 856, and one or more electrodes 860 may be mounted on either face 852, 856, or both. In some cases, a bonding material (for instance, an adhesive) may be placed between the first face 852 and the actuator 808 and/or adjacent to the second face (either between the second face 856 and the electrodes 860 or over the second face and the electrodes 860, or both.

Figure 8B:
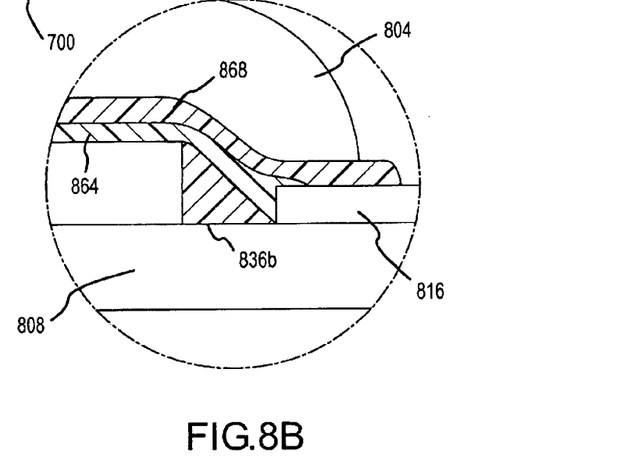

In some cases, one or more layers of bonding material may be disposed between and/or among the sealing member 804 and various components of the aerosol generator. As discussed above, one such bonding material may be an adhesive 844. Other bonding materials can include paints, epoxies, primers, and the like, as discussed herein. As illustrated by FIG. 8A, a first layer of bonding material 864 can be applied over the second face 856 of the vibratory element 812 and/or the electrode 860. The first layer 864 additionally can be disposed over any adhesive 836 adjacent to the outer 840 and/or inner 844 surfaces of the vibratory element. In some cases, as shown in FIGS. 8A and 8B, the adhesive 836 can be tapered, such that the first layer 864 can be applied to the point where the adhesive tapers to be flush with the actuator 808, forming a barrier over the vibratory element 812, the electrode 860, and any adhesive 836. Depending on the embodiment, any of the bonding materials used herein can be applied as the first layer 864. In a particular embodiment, the first layer 864 can be a paint and/or an epoxy.

Other embodiments can include one or more additional layers 868 of bonding material, which also can comprise any of the bonding materials discussed herein. The additional layers 868 can overlay the first layer 864 and can, additionally, be applied to portions of the actuator 808. As illustrated more clearly by FIG. 8B, in some cases, the first layer 864 can be applied flush with (or slightly overlapping) the aerosolizing element 816, such that the additional layers 868 can be applied over the first layer and a portion of the aerosolizing element 816. If desired, the additional layers 868 can also be applied around the outer surface 828 of the actuator and can cover at least a portion of the bottom face 824 of the actuator.

In some embodiments, the sealing member 804 can comprise an elastomer, including any of those discussed above. In a particular embodiment, the sealing member 804 may comprise silicone. A silicone that may be used in accordance with the present invention is a two part silicone, available from a company known as Wacker-Chemie GmbH, Geschaftsbereich Silicone, Hanns-Seidel-Platz 4, D-81737 Muchen (Munich, Germany). Such silicone is known to be described in a product description captioned "Elastosil ® LR 3003/10 A, B-LR 3003/80 A, B." One variety of such silicone that may be used in accordance with the present invention is designated as 40 Shore, representative of relative hardness of the cured silicone.

As noted above, in some embodiments, prior to molding the sealing member 804 about the aerosol generator, a layer of primer (which can be thought of as one of the layers 868 in FIG. 8A) may be applied to surfaces of the aerosol generator receiving the overmold, which can include the vibratory element, the electrode, the portions of the actuator, and a portion of the aerosolization element, such as the flange, or part of the flange. The primer may be applied to cover a slightly larger area than the overmold, to ensure that there is sufficient coverage of the primer to maximize bonding of the overmold. A primer that may be used in accordance with the present invention is known as CF6-135 High Technology Silicon Primer (Clear) available from a company known as NuSil Technology, Carpenteria, Calif., USA.

In other embodiments, a layer of epoxy (which can be thought of as the first layer 864 in FIG. 8A) may be applied to the exposed surfaces of the vibratory element. This layer can be applied prior to the application of a primer, or may be applied without the addition of a primer. The painted epoxy may comprise an autoclavable epoxy, such as, for example, a product designated as Masterbond EP3HTMED by a company known as Masterbond of New York, USA. The epoxy paint may be applied in a first layer and a second layer. In such case, it may be applied at room temperature with a fine point paintbrush. It may be cured at 130 degrees C. for 30 minutes, whereupon a second application may be applied at room temperature, and likewise cured at 130 degrees C. for 30 minutes.

It will be appreciated that the thickness of any bonding material (whether paint, primer, epoxy or the like) can be relatively small compared to the size of the aerosol generator and sealing member. As such, each bonding material may range from approximately a nanometer to approximately several micrometers in thickness, depending on the material used. Accordingly, in the various figures accompanying this application, the paint and primer thickness are enlarged for purposes of illustration.

Figure 9A:
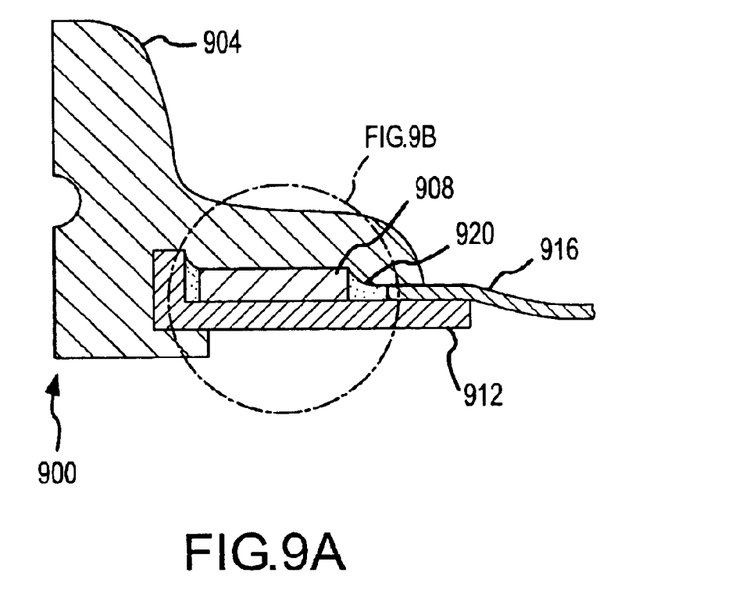
FIGS. 9A and 9B illustrate a portion of an aerosol generator assembly having an adhesive situated between an actuator and a vibratory element, in accordance with various embodiments of the invention.
Figure 9B:
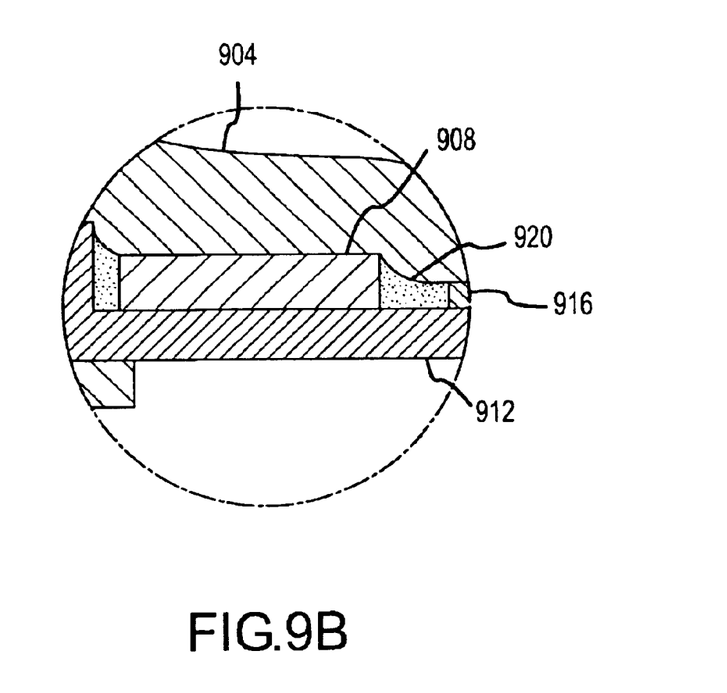

FIGS. 9A and 9B illustrate how an adhesive may be used in accordance with some embodiments of the invention. An aerosol generator assembly 900 may be formed of a sealing member 904 molded around an aerosol generator, which can comprise a vibratory element 908, an actuator 912 and an aerosolizing element 916. A relatively thin layer of adhesive 920, which can be an epoxy adhesive, can be disposed between the vibratory element 908 and the actuator 912. Excess adhesive may adhere to the sides of the vibratory element 908, and, in this way, can be used to provide a more secure fit between the sealing member 904 and the aerosol generator. Some embodiments, therefore, omit any additional bonding materials, as the adhesive 920 and sealing member act to provide a relatively impervious barrier between the surrounding environment and the vibratory element 908 (and, optionally, one or more electrodes, which are not shown in FIGS. 9A and 9B).

Figure 10:
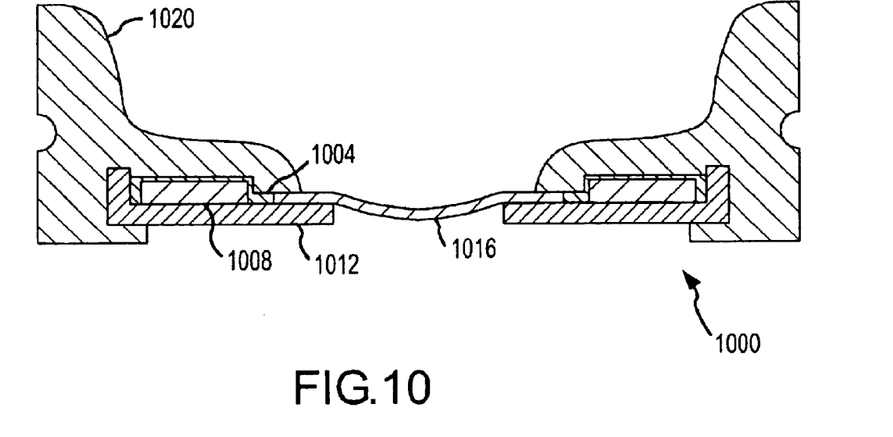
FIG. 10 illustrates a cross section of an aerosol generator assembly having a single layer of bonding material applied to portions of a vibratory element, in accordance with various embodiments of the invention.
Figure 11:
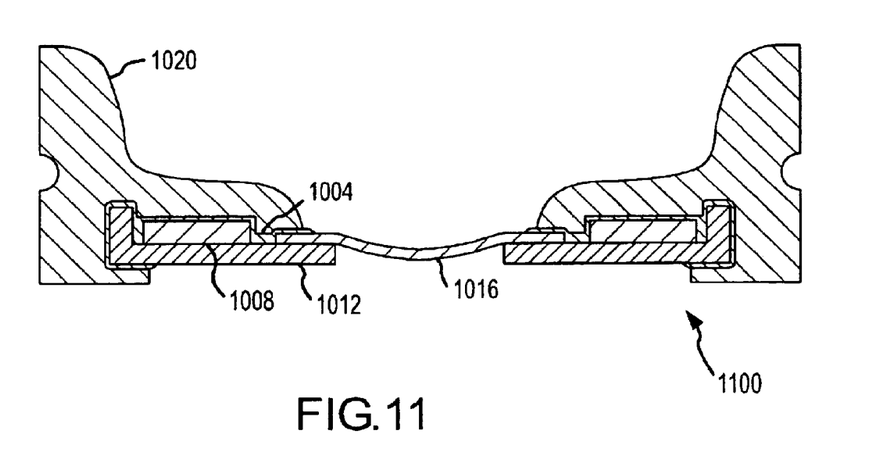
FIG. 11 illustrates a cross section of an aerosol generator assembly having a single layer of bonding material applied to portions of a vibratory element, an actuator and an aerosolization element, in accordance with various embodiments of the invention.

FIGS. 10–16 illustrate several different embodiments of the invention, employing a variety of bonding materials between and among the sealing member and various components of the aerosol generator. For ease of illustration, each of FIGS. 10–16 omit the electrodes, but those skilled in the art will appreciate, based on the disclosure herein, that electrodes could be incorporated as desired into each of the illustrated embodiments. Turning now to FIG. 10, an aerosol generator assembly 1000 is illustrated. The assembly includes a single layer 1004 of bonding material, which can be primer, paint, epoxy, etc., applied to the top face and each side face of a vibratory element 1008, which is mounted on an actuator 1012. Hence, the bonding material 1004, in conjunction with the actuator 1012, completely surrounds the vibratory element. In the assembly 1100 of FIG. 11, a layer of bonding material 1104 has been applied not only to surround the upper, inner and outer surfaces of the vibratory element 1008, but also has been applied to portions of the actuator 1012 (including the flange and bottom surface thereof), as well as to portions of the aerosolizing element 1016. Thus, the bonding material 1104 has been applied to every surface of the aerosol generator with which the sealing member 1020 comes into contact.

Figure 12:
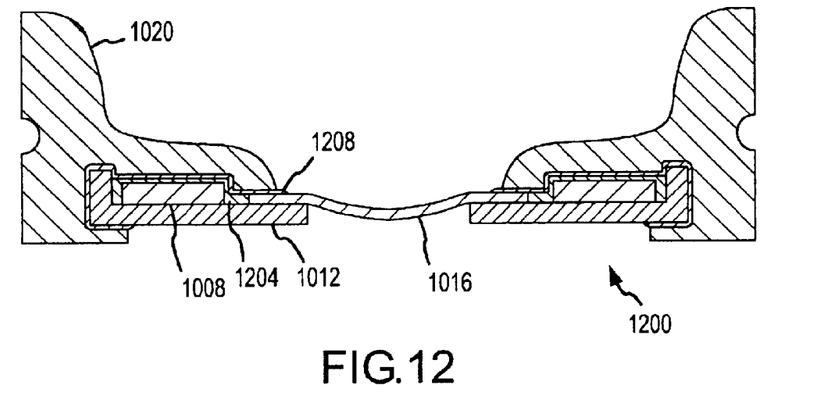
FIG. 12 illustrates a cross section of an aerosol generator assembly having a first layer of bonding material applied to portions of a vibratory element and a second layer of bonding material applied to portions of the vibratory element, an actuator and an aerosolizing element, in accordance with various embodiments of the invention.

FIG. 12 illustrates an aerosol generator assembly 1200 employing a first layer 1204 and a second layer 1208 of bonding material. The first layer 1204 has been applied to the top, inner and outer surfaces of the vibratory element 1008, similar to layer 1004 in FIG. 10. The second layer 1208 is applied over the top of the first layer 1204 and also to portions of the actuator 1216 (including, again, portions of the flange and bottom surfaces of the actuator), as well as to the outer portion of the aerosolizing element 1016. Hence, like the layer 1104 in FIG. 11, the second layer 1208 has been applied to every surface of the aerosol generator with which the sealing member 1020 comes into contact.

Figure 13:
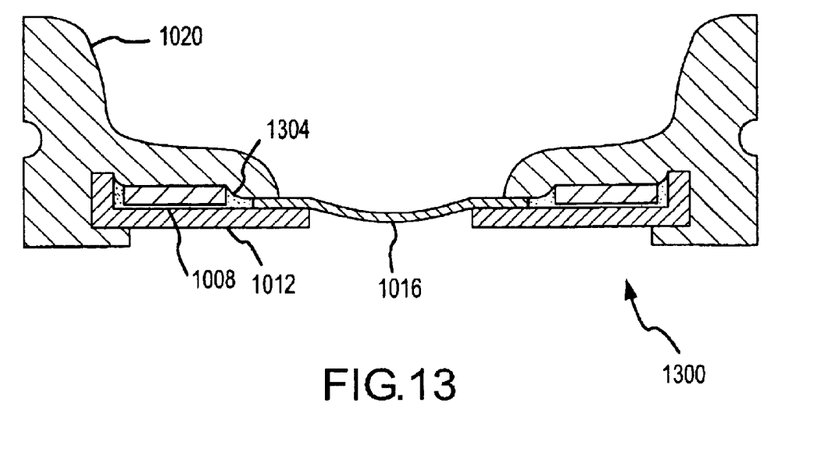
FIG. 13 illustrates a cross section of an aerosol generator assembly having an adhesive disposed between a vibratory element and an actuator, in accordance with various embodiments of the invention.
Figure 14:
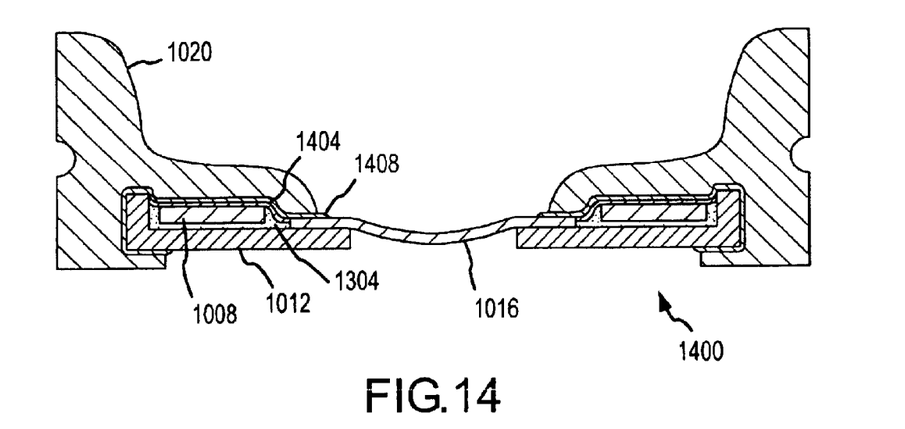
FIG. 14 illustrates a cross section of an aerosol generator assembly having an adhesive disposed between a vibratory element and an actuator, a first layer of bonding material applied to portions of the vibratory element, and a second layer of bonding material applied to portions of the vibratory element, the actuator, and an aerosolizing element, in accordance with various embodiments of the invention.
Figure 15:
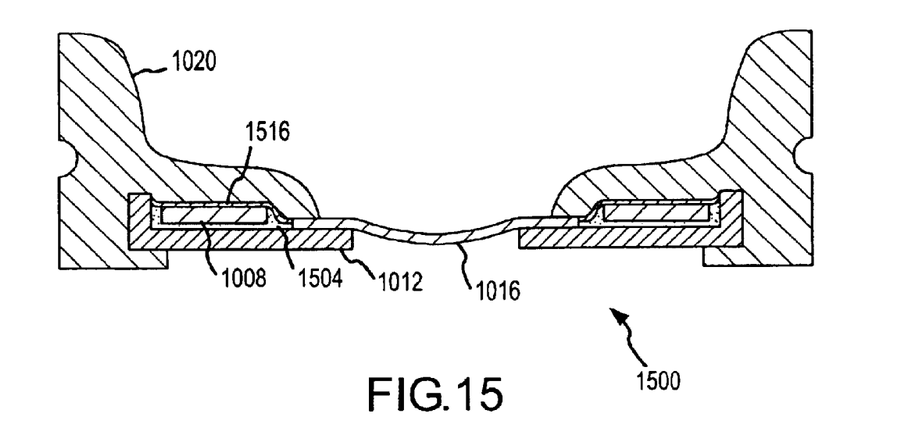
FIG. 15 illustrates a cross section of an aerosol generator assembly having an adhesive disposed between a vibratory element and an actuator and first layer of bonding material applied to portions of the vibratory element, in accordance with various embodiments of the invention.
Figure 16:
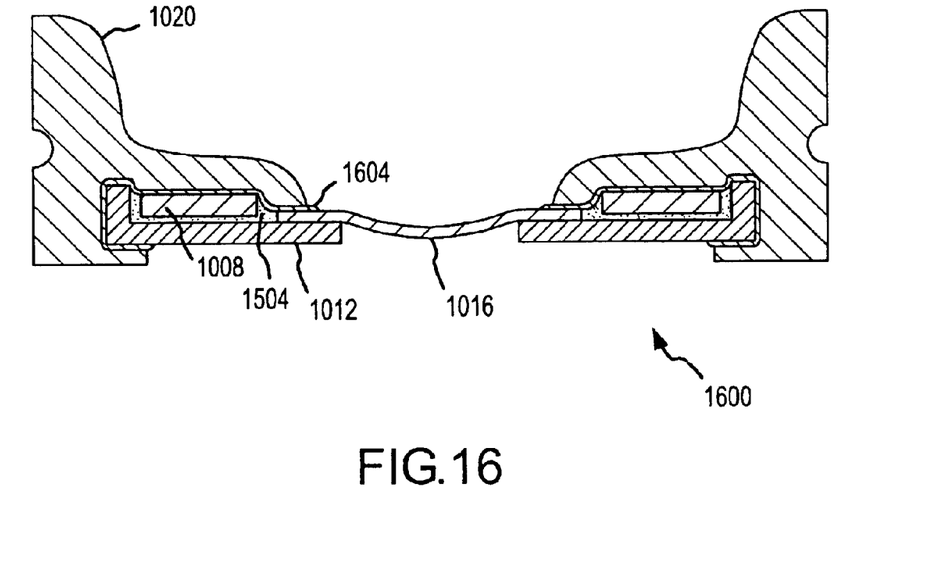
FIG. 16 illustrates a cross section of an aerosol generator assembly having an adhesive disposed between a vibratory element and an actuator and first layer of bonding material applied to portions of the vibratory element, the actuator, and an aerosolization element, in accordance with various embodiments of the invention.

FIG. 13 illustrates an embodiment of an aerosol generator assembly 1300 similar to that discussed with respect to FIGS. 9A and 9B, in which the bonding material 1304 (perhaps an adhesive) is applied between the vibratory element 1008 and the actuator 1012. In contrast, the assembly 1400 of FIG. 14 includes the adhesive 1304 between the vibratory element 1008 and the actuator 1012, as well as additional layers 1404 and 1408, which can be thought of as similar to layers 1204, 1208 respectively, illustrated in FIG. 12. FIG. 15 illustrates an aerosol generator assembly 1500 in which a layer of adhesive 1504 is disposed between the vibratory element 1008 and the actuator 1012. Further, a layer 1516 of bonding material overlays the adhesive 1504 and the vibratory element 1008, such that the adhesive 1504 and the layer 1516 of bonding material together function to completely encapsulate the vibratory element 1008. The assembly 1600 of FIG. 16 is similar to the assembly 1500 of FIG. 15, except that the layer of bonding material 1604 is applied not only to the adhesive 1504 and the vibratory element 1008, but also to portions of the actuator 1012 and aerosolizing plate 1016, effectively coating each surface that will be in contact with the sealing member 1020.

Figure 17:
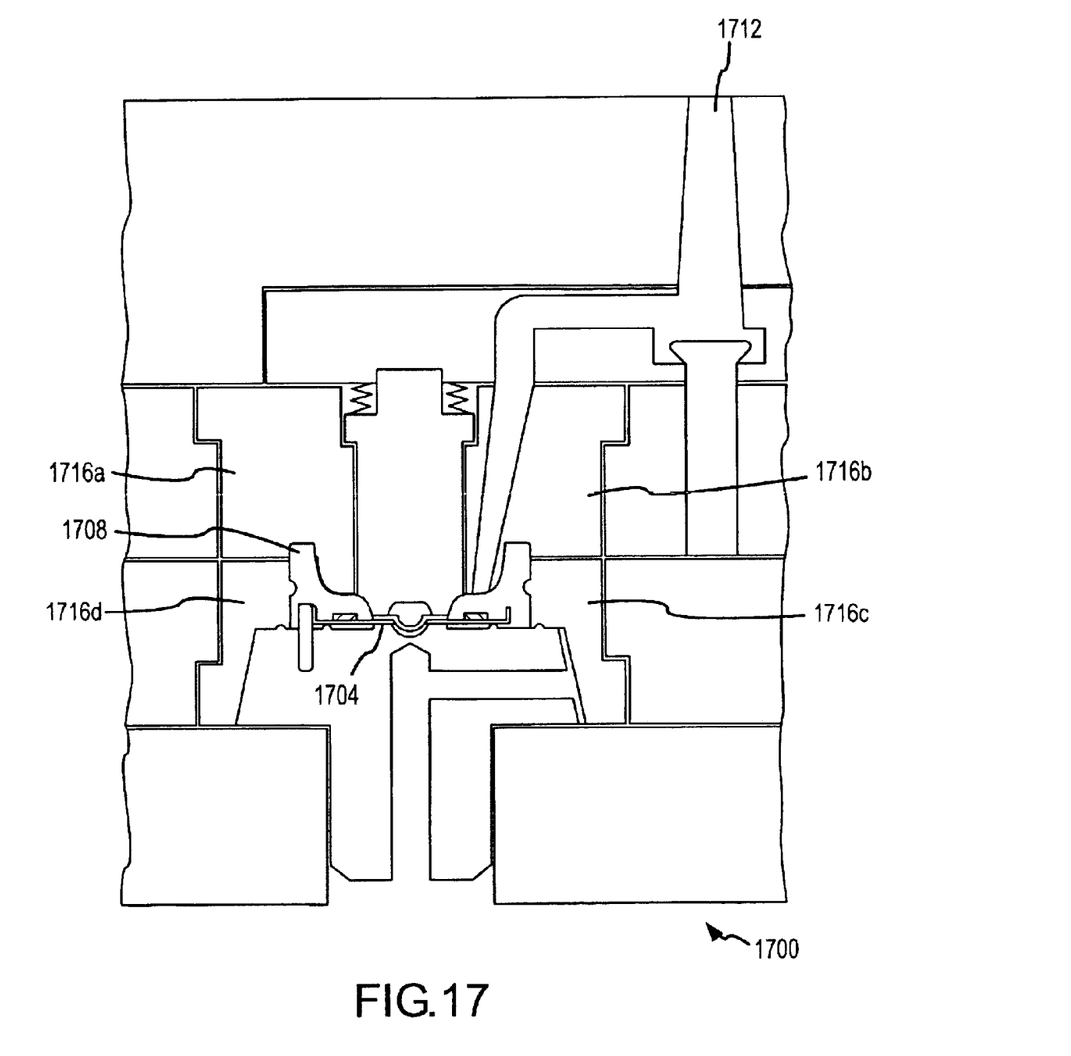
FIG. 17 illustrates a cross section of an aerosol generator disposed within a mold assembly, in accordance with embodiments of the invention.
Figure 18:
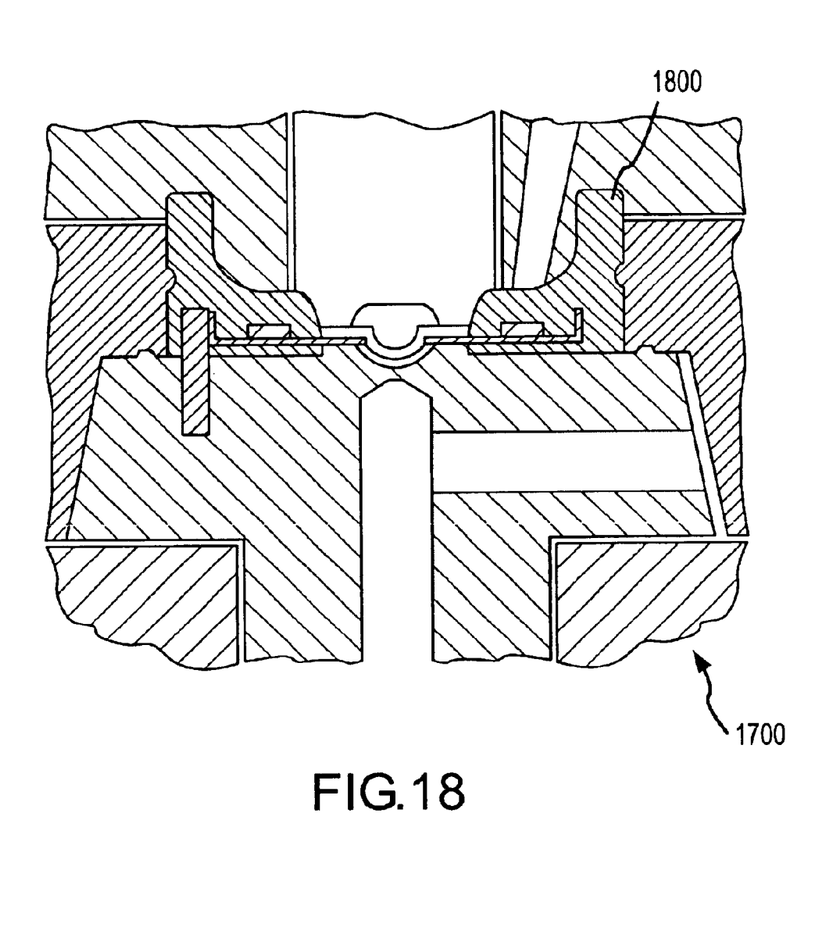
FIG. 18 illustrates a detail view of the aerosol generator and mold assembly of FIG. 17.

Turning now to the molding process, FIG. 17 illustrates an exemplary mold assembly 1700 for molding a sealing member onto an aerosol generator, in accordance with embodiments of the invention. The mold assembly 1700 is designed to accept an aerosol generator 1704 and defines a cavity 1708 into which mold material may be placed. The cavity defines the shape of the sealing member to be molded. In various embodiments, the mold material may comprise any of the materials discussed above with regards to the composition of a sealing member. In a particular embodiment, the mold material is capable of being injection molded. In other cases, the mold material can be in a liquid or semi-liquid form. The mold material can be placed into the cavity 1708 through any suitable method known in the art, including merely by way of example, injection molding via channel 1712. Those skilled in the art will appreciate that the mold assembly 1700 can comprise multiple components 1716a–d, which can be disassembled after the sealing member has hardened and/or cured, to allow for easy removal of the finished article. FIG. 18 illustrates a detail drawing of the mold assembly 1700 after mold material 1800 has been injected into the cavity.

Figure 19:
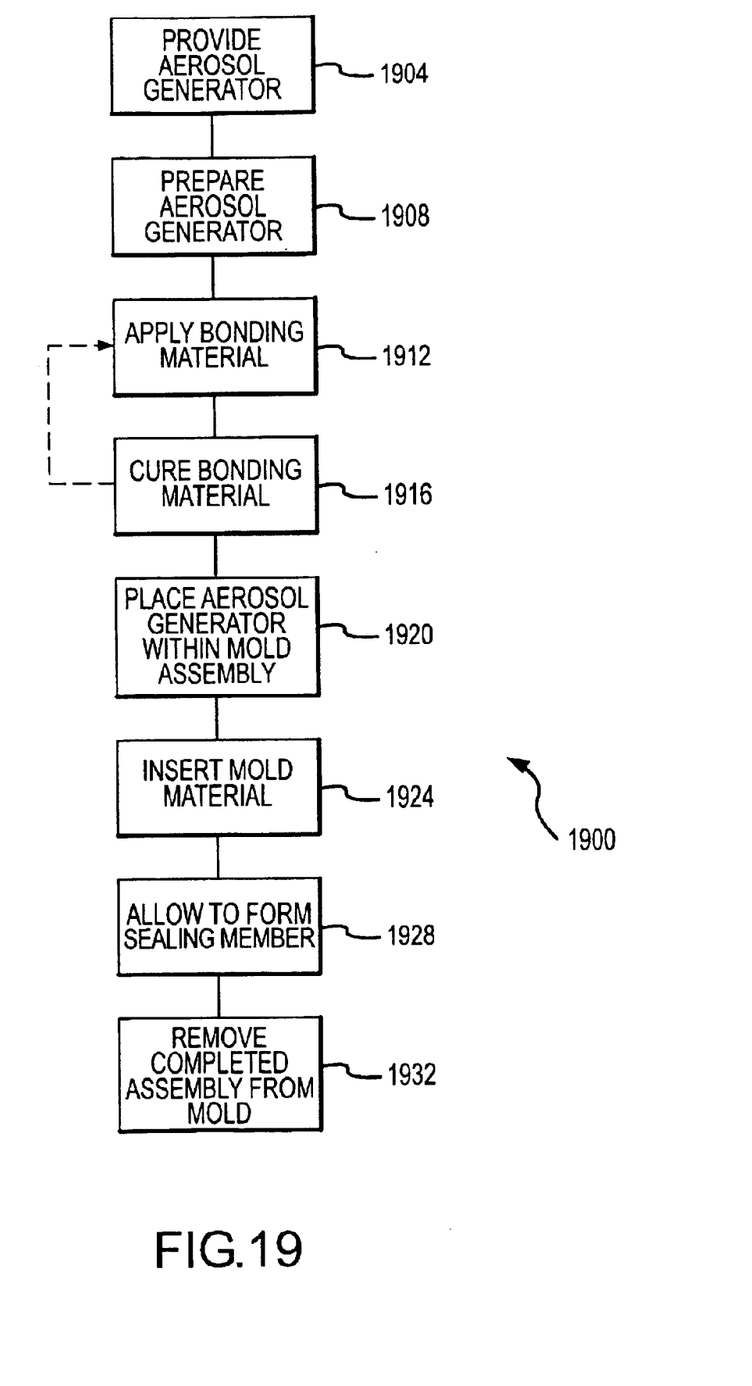
FIG. 19 illustrates a process flow diagram for producing an aerosol generator assembly in accordance with various embodiments of the invention.

Hence, certain embodiments of the invention provide methods for creating aerosol generator assemblies. One exemplary embodiment 1900 is illustrated by FIG. 19. It should be noted that, while the procedures in method 1900 are illustrated and discussed in a certain order for ease of description, embodiments of the invention are not limited to any particular order.

The method 1900 comprises providing a aerosol generator (block 1904), which can, in some embodiments, include any of the aerosol generators discussed herein. At block 1908, the aerosol generator can be prepared to receive a bonding material and or to be molded with a sealing member. Preparation can include, inter alia, priming, scoring, chemical etching, and the like. At block 1912, a layer of bonding material, such as adhesive, epoxy, paint, primer and/or the like can be applied, and at block 1916 that layer can be cured. In some cases, the application of the bonding material can be done by dipping, paintbrush, airbrush, and/or other known application techniques. In other cases, the curing process can take place at a relatively high temperature, for a specified period of time. Optionally, the application (block 1912) and/or curing (block 1916) procedures can be repeated as necessary to produce multiple layers of bonding material and/or a single, thicker layer of material.

At block 1920, the aerosol generator can be placed within a mold assembly, and at block 1924, mold material may be placed into one or more appropriate cavities in the mold assembly. As noted above, block 1924 can include any appropriate procedure, including injection molding, packing, and the like. The mold material can then be allowed to form (e.g., cure, harden, etc.) to produce a sealing member molded onto the aerosol generator (block 1928), at which point the finished aerosol generator assembly can be removed from the mold assembly (block 1932).

While the above is a detailed description of illustrative embodiments of the invention claimed herein, various alternatives, modifications, and equivalents may be employed without departing from the present invention. Thus, although the foregoing has been described in detail for purposes of illustration, it will appreciated that alternatives, modifications and equivalents may be practiced without departing from the invention and the invention herein is limited only by the appended claims.

What is claimed is:

1. An apparatus for generating an aerosol, comprising:
an actuator having a first face and a second face and defining an opening therethrough;
an aerosolization element mounted on the actuator and disposed substantially over the opening, wherein the aerosolization element defines at least one aperture therethrough;
a vibratory element in mechanical communication with the actuator; and
a sealing member configured to isolate the vibratory element from a surrounding environment;
wherein the vibratory element may be operated to vibrate to cause movement of the aerosolization element in such a manner that a liquid at a first face of the aerosolization element can be dispensed as an aerosol through the at least one aperture; and
wherein the sealing member comprises an elastomer.

2. The apparatus of claim 1, wherein the vibratory element is annular.

3. The apparatus of claim 1, wherein the vibratory element comprises a piezoelectric ceramic.

4. The apparatus of claim 1, wherein the sealing member is annular, covering at least a portion of the first face of the actuator, at least a portion of the second face of the actuator, and at least a portion of the vibratory element.

5. The apparatus of claim 1, wherein the elastomer comprises a rubber.

6. The apparatus of claim 5, wherein the rubber is a synthetic rubber.

7. The apparatus of claim 5, wherein the rubber is silicone.

8. The apparatus of claim 1, wherein the sealing member is molded around at least a portion of the vibratory element.

9. The apparatus of claim 8, wherein the sealing member is formed by injection-molding.

10. The apparatus of claim 1, further comprising at least one electrode coupled to the vibratory element.

11. The apparatus of claim 1, further comprising at least one layer of bonding material between the sealing member and the vibratory element.

12. The apparatus of claim 11, wherein the bonding material couples the sealing member relatively securely to at least one of the vibratory element and the actuator.

13. The apparatus of claim 11, further comprising at least one electrode coupled to the vibratory element, wherein the bonding material provides a relatively impervious barrier between the electrode and the surrounding environment.

14. The apparatus of claim 11, wherein the bonding material is relatively impervious to a relatively severe environmental condition.

15. The apparatus of claim 14, wherein the relatively severe environmental condition is selected from a group consisting of heat, humidity, pressure, alternating cycles of vacuum and pressure, and a corrosive chemical.

16. The apparatus of claim 11, wherein the bonding material is selected from the group consisting of a paint, an epoxy, an adhesive and a primer.

17. The apparatus of claim 11, wherein the at least one layer of bonding material comprises a first application of a first bonding material and a second application of a second bonding material.

18. The apparatus of claim 17, wherein the first and second bonding materials are the same bonding material.

19. The apparatus of claim 11, wherein the at least one layer of bonding material is applied room temperature and cured at a relatively high temperature for a specified period of time.

20. The apparatus of claim 19, wherein the relatively high temperature is above about 100 degrees C.

21. The apparatus of claim 20, wherein the relatively high temperature is between about 100 degrees C. and about 150 degrees C.

22. The apparatus of claim 21, wherein the relatively high temperature is between about 120 degrees C. and about 140 degrees C.

23. The apparatus of claim 22, wherein the relatively high temperature is about 130 degrees C.

24. The apparatus of claim 19, wherein the specified period of time is between about 15 minutes and about 45 minutes.

25. The apparatus of claim 24, wherein the specified period of time is about 30 minutes.

26. The apparatus of claim 11, wherein the bonding material further comprises an adhesive situated between the vibratory element and the actuator.

27. The apparatus of claim 26, wherein the vibratory element comprises an inner surface and an outer surface, and wherein the adhesive is further situated between the sealing member and at least a portion of at least one of the inner and outer surfaces of the vibratory element.

* * * * *